Dec. 4, 1962 F. W. ANDERSON Plant Pat. 2,198
CHERRY TREE
Filed Jan. 26, 1962
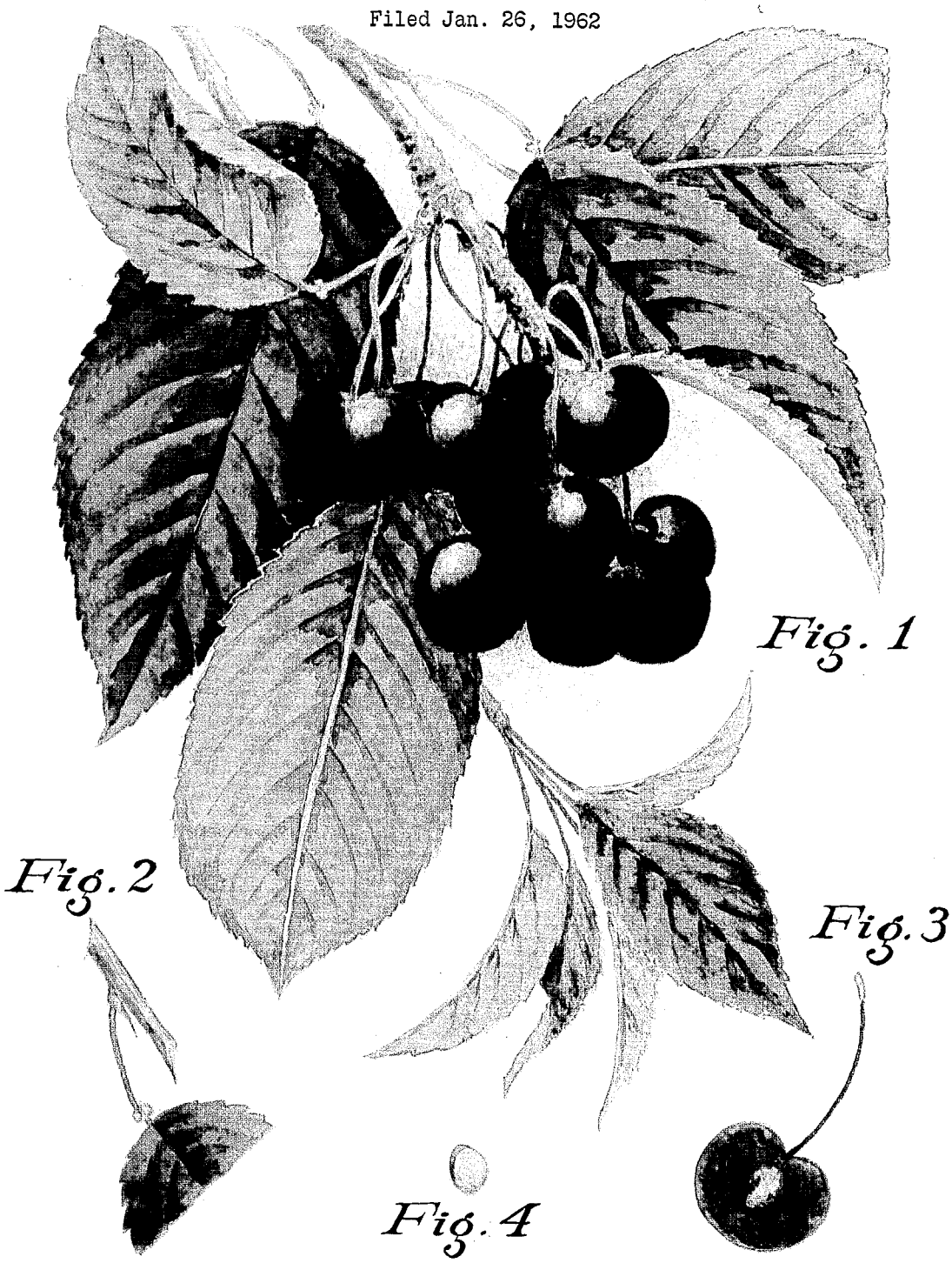
WITNESS
Addison E Avery
INVENTOR
Frederic W. Anderson
Webster & Webster
ATTYS.

United States Patent Office

Plant Pat. 2,198
Patented Dec. 4, 1962

2,198
CHERRY TREE

Frederic W. Anderson, Merced, Calif., assignor to Fowler Nurseries, Inc., Newcastle, Calif., a corporation Filed Jan. 26, 1962, Ser. No. 169,155
1 Claim. (Cl. 47—62)

This invention relates to a new and distinct variety of cherry tree which, while bearing general resemblance to the Bing (unpatented) in the size, appearance, and harvest period of the fruit, is distinctively characterized—in comparison—by a tree which is larger with longer, wider, and thicker leaves having a pubescent rather than glabrous petiole, and—more important—by greater production of the fruit, substantially no doubling of the fruit, and an absence of cracking thereof at ripening.

The present variety of cherry tree, which is a seedling of the Bing, but with the pollen parent unknown, was originated by me, in my experimental orchard located near Merced, California, in the following manner:

Several thousand seeds, from open pollinated flowers of the Bing, were planted and as the resultant seedlings matured and came into bearing—under conditions of careful observation and precise recording of their characteristics—one tree, and which is the instant variety, was recognized by me as having superior qualities in comparison to the Bing and in the respects hereinbefore described.

I have also accomplished asexual reproduction of the present variety by top-working on an older cherry tree in my experimental orchard located as aforesaid; such reproduction having run true, in all respects, to the parent tree.

In the drawings:

FIG. 1 is an elevation showing a cluster of cherries, together with twigs and leaves.

FIG. 2 is a fragmentary view of a leaf and its petiole; the view showing particularly the glands.

FIG. 3 is a sectional elevation of one of the cherries with the stone remaining in place.

FIG. 4 is a view of one of the stones removed from the fruit.

Referring now specifically to this new and distinct variety of cherry tree, the following is a detailed pomological description thereof in outline; all major color plate identifications being by reference to Maerz and Paul Dictionary of Color, except where otherwise indicated or where common terms of color definition are employed.

Tree:
- *Size.*—Large.
- *Vigor.*—Vigorous.
- *Form.*—Spreading.
- *Production.*—Very productive.
- *Bearing.*—Regular bearer.

Trunk:
- *Size.*—Stocky.
- *Texture.*—Medium.

Branches:
- *Size.*—Stocky.
- *Lenticels.*—Few; medium size.

Leaves:
- *Size.*—Large; average length—7"; average width—3".
- *Form.*—Ovate; acutely pointed.
- *Thickness.*—Thick.
- *Margin.*—Glandular; coarsely serrate.
- *Petiole.*—Long; thick; grooved; pubescent.
- *Glands.*—Average number and position—two on petiole, usually about one-quarter inch from base of blade; opposite; large; reniform; tinged red (4–L–5).
- *Color.*—Top side—medium green (22–L–8); under side—lighter green (21–J–6).

Flower buds:
- *Size.*—Large.
- *Length.*—Medium.
- *Form.*—Plump.

Flowers:
- *Blooming period.*—Substantially with the Bing; medium as compared with other varieties.
- *Color.*—White.

Fruit:
- *Maturity when described.*—Eating ripe, June 10, 1961.
- *Date of first picking.*—June 3, 1961.
- *Date of last picking.*—June 12, 1961.
- *Size.*—Uniform; large; average diameter axially—1"; average transversely in suture, plane—1⅛".
- *Form.*—Uniform; symmetrical; globose to slightly oblate; substantially no doubles.
- *Suture.*—Shallow.
- *Ventral surface.*—Rounded slightly.
- *Cavity.*—Wide; flaring.
- *Base.*—Rounded.
- *Apex.*—Slightly depressed.

Skin:
- *Thickness.*—Medium.
- *Texture.*—Tough to medium.
- *Tendency to crack.*—None.
- *Down.*—Wanting.
- *Color.*—Maroon (Sheet 185, Plate 1030, The British Colour Council, Horticultural Colour Chart), shading lighter in part.

Flesh:
- *Texture.*—Firm; crisp; meaty; melting.
- *Ripens.*—Even.
- *Flavor.*—Subacid.
- *Eating quailty.*—Good to best.
- *Color.*—Dark red or Indian Lake (Sheet 170, Plate 826, The British Colour Council, Horticultural Colour Chart).
- *Surface of pit cavity.*—Red.

Stone:
- *Type.*—Semi-free.
- *Size.*—Large; average length—7/16"; average breadth—5/16"; average thickness—¼".
- *Form.*—Oblong, with smooth surfaces.
- *Tendency to split.*—None.

*Use*: Market; local; dessert.
*Keeping quality*: Good.
*Shipping quality*: Good.

The tree and its fruit herein described may vary in slight detail due to climatic and soil conditions under which this variety may be grown; the present description being of the variety as grown in the Central Valley of California.

The following is claimed:

A new and distinct variety of cherry tree, as illustrated and described, bearing general resemblance to the Bing in the size, appearance, and harvest period of the fruit, but distinctively characterized in comparison by a tree which is larger with longer, wider, and thicker leaves having a pubescent petiole, and by greater production of fruit, substantially no doubling of the fruit, and an absence of cracking thereof at ripening.

No references cited.